United States Patent [19]

Klahr et al.

[11] 4,340,766

[45] Jul. 20, 1982

[54] DISHWASHING AGENTS AND CLEANING AGENTS CONTAINING OXYBUTYLATED HIGHER ALCOHOL/ETHYLENE OXIDE ADDUCTS AS LOW-FOAMING SURFACTANTS

[75] Inventors: Erhard Klahr, Ludwigshafen; Albert Hettche, Hessheim; Wolfgang Trieselt; Dieter Stoeckigt, both of Ludwigshafen; Horst Trapp, Plankstadt, all of Fed. Rep. of Germany

[73] Assignee: BASF Aktiengesellschaft, Ludwigshafen, Fed. Rep. of Germany

[21] Appl. No.: 227,280

[22] Filed: Jan. 22, 1981

[30] Foreign Application Priority Data

Feb. 14, 1980 [DE] Fed. Rep. of Germany ....... 3005515

[51] Int. Cl.$^3$ ....................... C07C 43/00; C07C 43/04

[52] U.S. Cl. .................................... 568/625; 568/624

[58] Field of Search ........................ 568/625, 624, 622

[56] References Cited

U.S. PATENT DOCUMENTS

| | | | |
|---|---|---|---|
| 2,674,619 | 4/1954 | Lundsted | 568/625 |
| 3,956,401 | 5/1976 | Scardera et al. | 568/625 |

FOREIGN PATENT DOCUMENTS

| | | | |
|---|---|---|---|
| 1814439 | 10/1969 | Fed. Rep. of Germany | 568/625 |
| 1767173 | 9/1971 | Fed. Rep. of Germany | 568/625 |

OTHER PUBLICATIONS

Publication—Relationship Between Chemical Constitution and Biological Degradation in Non-Ionic Detergents in Sixth International European Symposium, vol. III, p. 746 (1972) by W. K. Fisher.

*Primary Examiner*—Werren B. Lone
*Attorney, Agent, or Firm*—Oblon, Fisher, Spivak, McClelland & Maier

[57] ABSTRACT

Biodegradable and low-foaming cleaning agents and dishwashing agents containing non-ionic surfactants which have been obtained by reacting one or more adducts of a $C_8$–$C_{20}$-alkanol and from 4 to 14 moles of ethylene oxide with 1,2-butylene oxide in a molar ratio of from 1:1.6 to 1:2.4.

4 Claims, No Drawings

DISHWASHING AGENTS AND CLEANING AGENTS CONTAINING OXYBUTYLATED HIGHER ALCOHOL/ETHYLENE OXIDE ADDUCTS AS LOW-FOAMING SURFACTANTS

The present invention relates to low-foaming and biodegradable dishwashing agents and cleaning agents which contain non-ionic surfactants which have been obtained by oxyethylation of higher alcohols, followed by oxybutylation of the products.

At the present day, crockery and other articles of all kinds made of glass, china, ceramic or metal are in the main cleaned by mechanical washing processes. For this purpose, dishwashing agents containing special surfactants are employed, and these must be very low-foaming so as not to interfere with the operation of the dishwasher. Excessive foaming, caused by the vigorous agitation of the liquor in the machine, causes considerable problems, since the foam reduces the mechanical effect of the liquor sprayed onto the items being washed, and causes the machine to froth over.

An important category of non-ionic surfactants for the above purpose are the compounds referred to generally as ethylene oxide/propylene oxide block copolymers; such compounds are described in U.S. Pat. No. 2,674,619.

These surfactants exhibit low foaming and good dispersing power. However, they have a very low wetting power, and the biological degradability is far below the 80% prescribed in legislation in the Federal Republic of Germany and other countries.

German Laid-Open Application DOS No. 1,814,439 discloses low-foaming, non-ionic surfactants which are obtained by reacting not more than 1.5 moles of butylene oxide with an adduct of a higher alkanol and ethylene oxide, containing from 4 to 10 moles of ethylene oxide per mole of the alkanol.

However, it has been found that the surfactants proposed in this DOS are not entirely satisfactory in respect of low foaming under vigorous agitation of the liquor, and in the presence of large amounts of protein.

It is known, and does not require the quotation of literature references, that the reaction of an alcohol/ethylene oxide adduct with a higher alkylene oxide, eg. propylene oxide or butylene oxide, reduces foaming, the reduction being the greater, the larger the amount of such higher alkylene oxides employed.

However, the above problem of biological degradability shows a diametrically opposite trend to this, according to the existing literature.

For example, a report given by W. K. Fischer of Henkel, KGaA, to the VIth International Congress on Surfactants, 11th–15th Sept. 1972, in Zurich (see Volume III of the Congress Reports, page 746, loc.cit., FIG. 9), states that $C_{12}$–$C_{20}$-fatty alcohol/ethylene oxide adducts with 2 moles of butylene oxide as end groups exhibit absolutely unsatisfactory biological degradability according to the Henkel bottle test described in the said publication.

It is an object of the present invention to develop, specifically for technical cleaning processes, non-ionic surfactants which on the one hand are low-foaming and on the other hand are biodegradable to an extent which satisfies legal requirements.

We have found that, surprisingly, this object is achieved, contrary to the information in the above publication, with surfactants which have been obtained by reacting one or more adducts of a $C_8$–$C_{20}$-alkanol and from 4 to 14 moles of ethylene oxide with 1,2-butylene oxide in a molar ratio of from 1:1.6 to 1:2.4. The surfactants are at least 80% biodegradable, in accordance with legal requirements.

The products concerned are obtained by oxyethylating $C_8$–$C_{20}$-alkanols with from 4 to 14 moles of ethylene oxide and then oxybutylating the products with from 1.6 to 2.4 moles of butylene oxide.

According to our investigations, carried out in accordance with the specifications prescribed in the Bundesgesetzblatt, Part 1, page 244 et seq., of 30.1.1977, the surfactants are to be classified as satisfactorily biodegradable.

In accordance with the definitions given, starting materials for the preparation of the surfactants to be used according to the invention are fatty alcohols of 8 to 20 carbon atoms, or mixtures of such alcohols. The alcohols may be branched or straight-chain, but are preferably substantially straight-chain or only slightly branched. Examples of appropriate alcohols are octanol, nonanol, decanol, dodecanol, tetradecanol, hexadecanol and oxadecanol (stearyl alcohol), and mixtures of these. Alcohols obtained by the Ziegler synthesis or the oxo synthesis are industrially particularly preferred. These are $C_9/C_{11}$, $C_{13}/C_{15}$ or $C_{16}/C_{18}$ alcohol mixtures obtained by the oxo synthesis or, equally advantageously, $C_8/C_{10}$, $C_{10}/C_{12}$, $C_{12}/C_{16}$ or $C_{16}/C_{20}$ alcohol mixtures obtained by the Ziegler synthesis. Amongst the latter, the $C_{10}/C_{12}$ cut is particularly advantageous.

The alcohols are reacted with 4–14, preferably 5–11, moles of ethylene oxide. The oxyethylates thus obtained are then reacted with 1.6–2.4, preferably 2–2.4, moles of 1,2-butylene oxide per mole of oxyethylated alcohol.

The surfactants thus obtained constitute an optimum compromise between low foaming and not less than 80% biological degradability, as legally prescribed in the Federal Republic of Germany.

The surfactants to be used according to the invention are employed, for example, in the final rinse in commercial dishwashers.

For example, the final rinse formulation contains from 7 to 50% by weight, based on total formulation, of the novel surfactant, from 1 to 20% by weight of a diol, eg. glycol or propanediol, from 1 to 20% by weight of an alkylsulfonate, eg. a cumenesulfonate, and from 0 to 30% by weight of an acid component, eg. citric acid or an industrial acid mixture; industrially, a particularly important mixture of this type contains succinic acid, glutaric acid and adipic acid.

The surfactants to be used according to the invention can in particular be employed in industrial cleaning processes which, because of vigorous turbulence, may cause especially severe foaming; an example is conveyor-type dishwashers as used in the catering units of hotels and hospitals.

The Examples which follow illustrate the invention, without implying any limitation.

EXAMPLES

The cloud points were determined in accordance with DIN 53,917.

To obtain comparable foaming values, products of the same cloud point were used in each case.

The foaming characteristics of the surfactants were tested in a dishwasher in the presence of protein (egg test).

Egg test:

The number of revolutions of a spray arm in a dishwasher was determined by magnetic induction measurement, using a counter.

Foaming, which occurs particularly in the presence of proteins, reduces the speed of revolution of the spray arm. This reduction is an inverse measure of the suitability of the surfactant for dishwashers.

The test time was 12 minutes, the revolutions per minute being calculated, at certain intervals, from the total number of revolutions. The washing process was started at room temperature, and after about 10 minutes the water was at 60° C.

The biological degradability was determined as prescribed in the Bundesgesetzblatt, Part 1, page 244 et seq. (confirmatory test).

The results are shown in the Table which follows.

TABLE

| Product | | Cloud point in water, DIN 53,917 | Speed of spray arm in dishwasher in the presence of protein | Biological degradability Confirmatory test |
|---|---|---|---|---|
| $C_{13/15}$ Oxo-alcohol | 5.5EO + 1BO+ | 14° C. | 67 rpm | >80% |
| $C_{13/15}$ Oxo-alcohol | 4.3EO + 4PO | 14° C. | 60 rpm | >80% |
| $C_{13/15}$ Oxo-alcohol | 7EO + 2.4BO | 14° C. | 83 rpm | >80% |
| $C_{10/12}$-Alfol | 5.5EO + 1BO | 20° C. | 53 rpm | >80% |
| $C_{10/12}$-Alfol | 3.8EO + PO | 20° C. | 55 rpm | >80% |
| $C_{10/12}$-Alfol | 7EO + 2BO | 20° C. | 65 rpm | >80% |
| $C_{13/15}$ Oxo-alcohol | 5EO + 1BO | 6° C. | 80 rpm | >80% |
| $C_{13/15}$ Oxo-alcohol | 6.0EO + 2.4BO | 6° C. | 96 rpm | >80% |
| $C_{10/12}$-Alfol | 7.5EO + 1BO | 43° C. | 42 rpm | >80% |
| $C_{10/12}$-Alfol | 10.3EO + 2BO | 43° C. | 65 rpm | >80% |
| $C_{10/12}$-Alfol | 11EO + 2.4BO | 43° C. | 75 rpm | >80% |

+BO = butylene oxide
EO = ethylene oxide

The Table shows that the adducts to be used according to the invention combine good biological degradability with optimum low-foaming properties.

We claim:

1. A biodegradable and low-foaming cleaning and dishwashing agent containing non-ionic surfactants based upon ethoxylated and butoxylated alcohols, said non-ionic surfactants consisting of one or more adducts of a $C_8$- to $C_{20}$-alkanol and from 4 to 14 moles of ethylene oxide with 1,2-butylene oxide in a molar ratio of from 1:1.6 to 1:2.4.

2. The agent of claim 1, wherein said alkanol is a straight-chain alkanol.

3. The agent of claim 1, wherein said alkanol is a $C_{10}$- to $C_{12}$-alkanol.

4. The agent of claim 1, wherein said non-ionic surfactants consist of one or more adducts of a $C_8$- to $C_{20}$-alkanol and from 5-11 moles of ethylene oxide with 1,2-butylene oxide in a molar ratio of from 1:2 to 1:2.4.

* * * * *